United States Patent [19]

Nielsen et al.

[11] 4,061,659

[45] Dec. 6, 1977

[54] PROCESS FOR THE PRODUCTION OF ETHYLENE OXIDE

[75] Inventors: Robert P. Nielsen; Peter A. Kilty, both of Houston, Tex.

[73] Assignee: Shell Oil Company, Houston, Tex.

[21] Appl. No.: 700,642

[22] Filed: June 28, 1976

[51] Int. Cl.$^2$ ............................................ C07D 301/10
[52] U.S. Cl. ................................................. 260/348.34
[58] Field of Search ................................. 260/348.5 R

[56] References Cited

U.S. PATENT DOCUMENTS

| 3,207,700 | 9/1965 | Saffer | 252/443 |
| 3,725,307 | 4/1973 | Brown | 252/455 |

FOREIGN PATENT DOCUMENTS

| 211,242 | 6/1956 | Australia | 260/348.5 R |

Primary Examiner—Norma S. Milestone

[57] ABSTRACT

An improved process for the production of ethylene oxide by catalytic oxidation of ethylene is disclosed wherein reactant ethylene and an oxygen-containing gas are passed through a reaction zone containing a fixed catalyst bed comprising a supported silver catalyst, optionally diluted with an inert refractory particulate, at ethylene oxide forming conditions and the reaction product formed thereby is passed through a cooling zone adjacent to the reaction zone which is filled with an inert refractory particulate, whereby at least partial cooling of the reaction product is effected. In this improved process, the isomerization of ethylene oxide product to acetaldehyde and concomitant yield losses of ethylene oxide are substantially reduced by the use of an inert refractory particulate material having a surface area of 0.1 m$^2$/g or less in the cooling zone and, optionally, as an inert diluent in the catalyst bed of the reaction zone.

9 Claims, No Drawings

PROCESS FOR THE PRODUCTION OF ETHYLENE OXIDE

BACKGROUND OF THE INVENTION

This invention relates to an improved process for preparation of ethylene oxide by the partial oxidation of ethylene by means of gaseous oxygen in the presence of a silver containing catalyst. More particularly, this invention is directed to an improvement in the vapor phase oxidation of ethylene to ethylene oxide over a fixed catalyst bed of refractory support carrying active silver wherein the reaction zone effluent is immediately subject to cooling in a cooling zone filled with an inert particulate having a critically low surface area which minimizes isomerization of ethylene oxide to acetaldehyde.

The desirability of minimizing isomerization of ethylene oxide to acetaldehyde in conventional processes for direct oxidation of ethylene to ethylene oxide has long been recognized in the art. In such processes, which typically employ one or more tubular reactors containing fixed beds of silver catalyst on a refractory support, it is known that acetaldehyde is rapidly converted to carbon dioxide and water under ethylene oxide forming conditions. Further, any significant quantity of acetaldehyde not oxidized in the reaction zone appears as an unwanted impurity in the reaction product which must be rejected in downstream processing operations to meet product quality specifications. Thus, unless acetaldehyde formation is minimized, it can become a major factor contributing to ethylene oxide yield losses in the process as well as a troublesome product unpurity which increases the costs of downstream product processing and purification.

Since the high temperature conditions employed in the catalytic reaction zone appear to be particularly condusive to the isomerization of ethylene oxide to acetaldehyde and rapid combustion of the acetaldehyde formed to carbon dioxide and water, it is advantageous to effect rapid cooling of the reaction product as it leaves the reaction zone. To this end, typical commercial scale processes for catalytic oxidation of ethylene to ethylene oxide sometimes employ a post cooling section immediately downstream of the reaction zone to at least partially cool the reaction product to temperatures below those required for oxidation. This post cooling section may be packed or unpacked and is typically located adajcent to the reaction zone, very suitably as an extension to, or part of, the tubular reaction zone, itself. Since the use of packing in the post cooling section functions to reduce the residence time of the reaction zone effluent at the high temperatures required for ethylene oxide formation, there is good reason to prefer a packed cooling section over one which is unpacked. However, packings which have been used previously, including, typically, the catalyst carrier materials employed in the reaction zone, tend to promote the isomerization of ethylene oxide under the conditions which exist at the outlet of the reaction zone i.e., high temperature coupled with higher concentrations of ethylene oxide. These carrier materials, which are generally particulate refractory oxides having surface areas of at least 0.2 $m^2/g$, apparently possess a certain activity for ethylene oxide isomerization. As a result, the benefits obtained through reduced residence time with packing materials previously employed are substantially diminished by increases in the rate of ethylene oxide isomerization attributable to the packing material. Thus, it would be desireable if an inert packing material could be found which would give all the benefits of reduced residence time in the past cooling zone with little or no increase in the rate of ethylene oxide isomerization.

SUMMARY OF THE INVENTION

It has now been found that the rate at which ethylene oxide is isomerized and lost from the catalytic reaction zone effluent of conventional processes for direct oxidation of ethylene to ethylene oxide can be substantially reduced during passage of the effluent through a packed cooling zone located adjacent to the reaction zone, if the packing material employed is an inert refractory particulate having a surface area of 0.1 $m^2/g$ or less. This finding that the activity which so-called inert refractory material posses for isomerization of ethylene oxide is substantially surface area dependent and that a critical maximum limit exists for surface area below which truly inert materials are obtained is quite important both in reducing troublesome acetaldehyde formation and increasing the flexibility of the process conditions employed in the reaction zone of the process. That is, with the use of a truly inert packing material in the post reaction cooling section, it now becomes possible to use extended depths of packing in the cooling zone adjacent to the reaction zone thus lowering the exit gas temperature. This, in turn, allows the exit gas to contain a higher concentration of unreacted oxygen without encountering operating problems due to combustion. By raising the oxygen concentration in the reactant feed, higher overall selectivities and productivities in the conversion of ethylene to ethylene oxide may be obtained. Other advantages accrue from the discovery of a truly inert particulate solid packing material. For example, there are instances where it may be highly desireable to stage the silver catalyst concentration in the fixed bed of the reaction zone by mixing the active catalyst particles with an inert solid diluent i.e., avoidance of hot spots by incrementally increasing the catalyst concentration in the direction of the process flow. In these, cases, the inert refractory particulate materials of the instant invention make it possible to obtain such staging of the catalyst concentration in the reaction zone without encountering excessive isomerization and yield losses of ethylene oxide. This optional application of the inert refractory particulate material of critically low surface area according to the invention as an inert solid diluent in the reaction zone forms another embodiment of the invention.

Accordingly, the instant invention provides an improved process for the production of ethylene oxide by catalytic oxidation of ethylene wherein ethylene and an oxygen-containing gas are passed through a reaction zone containing a fixed catalyst bed comprising a supported silver catalyst, optionally diluted with an inert refractory particulate material, at ethylene oxide forming conditions and the reaction product formed thereby is passed through a cooling zone adjacent to the reaction zone, said cooling zone being filled with an inert refractory particulate material, characterized by the employment of an inert refractory particulate material having a surface area of 0.1 $m^2/g$ or less in the cooling zone and, optionally, as an inert diluent in the catalyst bed of the reaction zone.

DESCRIPTION OF THE PREFERRED EMBODIMENTS

The improvement according to the invention is applicable to any conventional process for the direct oxidation of ethylene to ethylene oxide where a supported silver catalyst is employed as a fixed catalyst bed in the reaction zone and the reaction product is at least partially cooled in a packed cooling zone located immediately downstream of, and adjacent to, the reaction zone. The conditions for carrying out the controlled oxidation of ethylene to ethylene oxide in the reaction zone broadly comprise those described in the prior art. This applies, for example to suitable temperature, pressures, residence times and diluent materials such as nitrogen, carbon dioxide, steam, argon, methane or other saturated hydrocarbons. Also contemplated are other conventional process conditions and modes of process operation such as the presence or absence of moderating agents to control the catalytic action, for example 1,2-dichloroethane, vinyl chloride or chlorinated polyphenyl compounds; the desireability of employing recycle operation or applying successive conversion in different reactors to increase the yields of ethylene oxide and any other special reaction zone conditions which may be selected in processes for preparing ethylene oxide. In such conventional processes, the controlled oxidation reaction is carried out at temperatures in the range of, for example from about 150 to about 450° C and preferably in the range of about 200° to about 300° C. From the standpoint of product yield, ethylene selectivity, catalyst life and ease of process control, it is most preferred to carry out the oxidation reaction at a temperature in the range of 225° C to 270° C. The reaction zone pressures employed for this vapor phase reaction generally range from about atmospheric to about 35 atmospheres, although higher pressures are not precluded. The oxygen containing gas employed is suitably a concentrated oxygen stream comprising oxygen in major amount with lesser amounts of one or more diluents such as nitrogen, argon, etc., or another oxygen-containing stream such as air. Preferably the oxygen reactant is relatively pure molecular oxygen with oxygen-containing gas streams having oxygen concentrations of not less than 95m percent being most preferred.

The catalyst employed in the fixed bed of the reaction zone may comprise any of the supported silver metal-containing catalyst disclosed in the prior art capable of catalyzing the controlled oxidation with molecular oxygen of ethylene to ethylene oxide. These comprise the catalysts consisting essentially of silver metal upon a suitable solid porous refractory support. Suitable supports are conventional refractory materials of natural or synthetic origin, preferably those having a macroporous structure, that is, a structure having a surface area below about 10 m$^2$/g and preferably below about 5 m$^2$/g. These support materials typically have an "apparent porosity" of greater than 20%. Very suitable supports comprise those of siliceous and/or aluminous composition. Specific examples of suitable supports are the aluminum oxides (including the materials sold under the trade name "Alundum"), charcoal, pumice, magnesia, zirconia, kieselguhr, fuller's earth, silicon carbide, porous agglomerates comprising silicon and/or silicon carbide, magnesia, selected clays, artificial and natural zeolites, metal oxide gel-type materials comprising oxides of heavy metals such as molybdenum, tungsten and the like, ceramics, etc. Aluminous materials, in particular those containing alpha alumina, are preferred. These alpha alumina support materials suitably have B.E.T. specific surface areas of from about 0.15 to 0.6 m$^2$/g and apparent porosities of from 46% to 52%. The B.E.T. method for determining specific surface area is described in detail in Brunauer, S., Emmet, P.H., and Teller, E., J. Am. Chem. Soc., 60 309-16 (1938). The supported silver catalysts employed in the reaction zone suitably contain from 2 to 20% by weight silver as a surface deposit. These catalysts may be prepared by a variety of techniques which are disclosed in the prior art, e.g., see U.S. Pat. No. 3,043,854, 3,575,888 and 3,702,259. The finished catalyst is a particulate material in the form of chunks, tablets, rings, pellets or the like of a size suitable for use in fixed bed operations.

The packed cooling zone which is employed to at least partially cool the reaction zone effluent in the process of the invention is positioned immediately downstream from, and adjacent to, the reaction zone. In typical operation, the reaction zone may comprise one or more tubular reactors in parallel or series filled with fixed beds of catalyst particles and externally cooled with a conventional coolant such as Dowtherm or water which is circulated or boiled in external contact with the tube or tubes containing the process flow. With this type of reactor, the packed cooling zone is suitably an intergral part of the downstream end portion of the reactor tube being comprised of either a tubular extension to the reaction zone or a portion of the reaction zone itself which is packed with inert refractory rather than catalyst. The packed cooling zone is also cooled externally with a conventional coolant and preferably is surrounded by a discrete, separately-cooled jacket (separate from the reaction zone coolant system). As a general matter, it is desireable to provide sufficient cooling in this packed cooling zone such that the reaction zone effluent is brought to a temperature of below about 200° C and preferably below about 150° C on exit from the cooling zone. At temperatures below 150° C, the possibility of further isomerization and/or oxidation reactions occurring in the product effluent is substantially reduced. In fact, the problems associated with combustion (formation of a flame front in the reaction zone effluent) are sufficiently diminished that the reactant oxygen concentration can be increased by about 1-2% units by volume based on the total reactant effluent as compared to operation without post cooling and without encountering undue problems in operation. In the process according to the invention, the packed cooling zone suitably comprises about 1 to 15% of the total catalyst bed length and preferably 1-10% of the total bed length.

To obtain the advantages of reduced isomerization and ethylene oxide yield losses with the improvement according to the invention, it is essential that an inert refractory particulate material having a surface area of about 0.1 m$^2$/g or less, as measured by the B.E.T. method, be employed as the packing material in the packed cooling zone. Suitable low surface area refractory materials in this regard include combinations of silica and alumina, aluminas, silicon carbide, alkali and alkaline earth metal modified silica aluminas (Mullite), ceramic materials and glass-type materials such as sodium polysilicate containing a stoichometric excess of silica. Preferred inert refractory materials according to the invention are those having surface areas below about 0.05 m$^2$/g with silicon carbide and combinations of silica and alumina especially in particular those containing a major porportion of silica, being particularly preferred. Most preferred are refractory materials having surface areas below about 0.01 m²/g. The inert refractory particulate packing materials of the invention may be of any conventional form or shape previously employed in packing applications including spheres, rings, tablets, chunks, pellets, strands and the like. Preferably the inert packing material is a formed particulate such as spheres or rings of a size similar to that of the catalyst support particles employed in the fixed bed of the reaction zone.

In an alternative embodiment of the invention, the inert refractory particulate, as defined above, is advantageously employed as a solid diluent in the fixed catalyst bed of the reaction zone. With this optional application of the inert refractory particulate material, it is possible by the use of appropriate catalyst loading procedure to stage the catalyst concentration in the reaction zone in any desired fashion without encountering undue product (ethylene oxide) isomerization and concomitant yield losses. This staging of the catalyst concentration is typically carried out by thoroughly premixing selected quantities of active catalyst particles and inert diluent and charging the admixture to the tubular reaction zone to achieve a catalyst concentration gradiant across the bed, based on bed volume. In cases where two or more tubular reactors are employed in series, the catalyst concentration may be staged by the addition of inert solid diluent such that the catalyst concentration differs from one tubular reactor to the next but remains constant within individual reactors. Alternatively, the catalyst concentration is staged within each tubular reaction zone by segregating the reaction zone into sections having different ratios of active catalyst to solid diluent. Preferably, the reaction zone is divided into two or more sections of increasing catalyst concentration in the direction of the process flow. In typical applications, the concentration of active catalyst particles are diluted about 25% to 75% in the first (up stream) one quarter to half of the bed length followed by subsequent dilutions of 0 to 50% in the remaining bed sections.

ILLUSTRATIVE EMBODIMENT I

A series of tests were carried out to determine the activity which various refractory particulate materials exhibit for ethylene oxide isomerization at an ethylene oxide concentration approximating that of a typical reactor product stream. In this test series, a 5% ethylene oxide in helium feed stream was passed through a tubular reactor packed with different refractory particulates at a temperature approximating that conventionally employed in the catalytic oxidation zone (260° C) and the amount of ethylene oxide converted was determined by Gas-Liquid Chromatography (GLC) analysis of the reactor effluent. Subsequent product analysis in each case showed the predominant conversion product to be acetaldehyde. Procedurally, the tests were carried out by charging three gram portions of the candidate particulate (crushed and screened to a 14/30 mesh) to a ¼ inches stainless steel tubular reactor, followed by heating of the reactor under helium flow until a stable temperature was maintained and the desired reaction temperature (260° C). At this point the feed containing 5% ethylene oxide was passed through the reactor at atmospheric pressure and a feed rate of 300 cc gas/hr/g of material tested. GLC samples were taken after 5 minutes to measure the conversion or loss of ethylene oxide by isomerization to acetaldehyde. The results of the rests, as well as an identification of the particulate materials tested is given in Table I below.

TABLE I

| Particulate tested | Composition %w Al₂O₃ | SiO₂ | Other | Surface Area m²/g | % Conversion of Ethylene Oxide |
|---|---|---|---|---|---|
| Silica-Alumina | 20 | 75 | — | <0.01 | 1.9 |
| Alumina | 99.5 | 0.3 | — | 0.22 | 3.1 |
| Alumina | 96 | 3 | — | 0.5 | 7.8 |
| Alumina | 99.5 | 0.3 | — | 1.1 | 29.1 |
| Alumina | 96 | 3 | — | 6.5 | 66 |
| Silica-Alumina | 83 | 15 | — | 53 | 100 |
| Alumina | 99+ | — | — | <0.4 | 4.5 |
| Alumina | 99+ | — | — | 0.16 | 0.7 |
| Silicon Carbide | 4.5 | 14.5 | 78% Silicon Carbide | 0.1 | 0.6 |
| Pyrex Glass Wool | — | — | a) | 0.01 | Trace | a)Sodium polysilicate containing a stoichiometric excess of silica.

ILLUSTRATIVE EMBODIMENT II

In this test series, several refractory particulates of different surface areas were evaluated as inert solid diluents in the fixed catalyst bed of the reaction zone under conditions typically employed for direct oxidation of ethylene to ethylene oxide in conventional processes. With this test procedure, a mixture containing from one to three grams of crushed and screened (14/20 mesh) candidate particular material and two grams of a commercial, crushed and screened (14/10 mesh) silver catalyst were placed in a bench-scale reactor. A feed composed of 30%m ethylene, 30%m methane, 9%m oxygen, and 31%m nitrogen was passed over the mixture at a temperature in the range 250–260° C; a pressure of 200 psig was used, with GHSV = 3300 hr⁻¹. Approximately 50% of the oxygen is converted under these conditions. The selectivity to ethylene oxide was determined by analysis of the product stream by GLC. The effect of the inert material on selectivity was measured by the (normalized) difference between the results obtained with and without the inert material being present. The results of the tests including particulate characterization are reported in Table II, below.

TABLE II

| Particulate Tested | Compositon % w Al₂O₃ | SiO₂ | Surface Area m²/g | Selectivity Loss % (±0.5%) |
|---|---|---|---|---|
| Silica-Alumina | 20 | 75 | <0.01 | 0 |
| Alumina | 99.5 | 0.3 | <0.01 | −0.03 |
| Alumina | 96 | 3.0 | 0.5 | −0.7 |
| Alumina | 99.5 | 0.3 | 0.2 | −0.9 |
| Alumina | 99.5 | 0.3 | 0.2 | −1.0 |
| Alumina | 99.5 | 0.3 | 0.3 | −1.5 |
| Alumina | 99.5 | 0.3 | 1.1 | −9.8 |
| Alundum | 83 | 15 | 14 | −79 |

What is claimed is:

1. In a process for the production of ethylene oxide by catalytic oxidation of ethylene wherein ethylene and an oxygen-containing gas are passed through a reaction zone containing a fixed catalyst bed comprising a supported silver catalyst, at ethylene oxide forming conditions and the reaction product formed thereby is passed through a cooling zone adjacent to the reaction zone, said cooling zone being filled with an inert refractory particulate material; the improvement which comprises, employing an inert refractory particulate material having a surface area of 0.1 m²/g or less in the cooling zone.

2. The process according to claim 1 wherein the supported silver catalyst in the fixed bed of the reaction zone is diluted with an inert refractory particulate material having a surface area of 0.1 m²/g or less.

3. The process according to claim 1, wherein the reaction product is cooled to a temperature below about 200° C in the cooling zone.

4. The process according to claim 3, wherein the reaction product is cooled to a temperature below about 150° C in the cooling zone.

5. The process according to claim 4, wherein the inert refractory particulate material is selected from the class consisting of silica-alumina, alumina, silicon carbide and glass-type materials.

6. The process according to claim 5, wherein the inert refractory particulate material has a surface area below about 0.05 m²/g.

7. The process according to claim 6, wherein the inert refractory particulate is a silica-alumina.

8. The process according to claim 3, wherein the cooling zone comprises the downstream end portion of a tubular reaction zone.

9. The process according to claim 8, wherein the cooling zone makes up about 1 to 15% of the total catalyst bed length in the tubular reaction zone.

* * * * *